United States Patent [19]
Muri et al.

[11] Patent Number: 5,766,215
[45] Date of Patent: Jun. 16, 1998

[54] ELECTROSURGICAL LOOP PROVIDING ENHANCED TISSUE COAGULATION

[75] Inventors: John Muri, Laguna Hills; Ralph Kenton Brady, Capistrano Beach; Gregory Lee Kelly, Laguna Niguel, all of Calif.

[73] Assignee: Endocare, Inc., Irvine, Calif.

[21] Appl. No.: 534,494

[22] Filed: Sep. 27, 1995

[51] Int. Cl.$^6$ ............................................. A61B 17/39
[52] U.S. Cl. ............................ 606/46; 606/41; 606/49
[58] Field of Search ............................ 606/46, 45, 41, 606/49

[56] References Cited

U.S. PATENT DOCUMENTS

| | | | |
|---|---|---|---|
| 5,354,296 | 10/1994 | Turkel | 606/41 |
| 5,395,363 | 3/1995 | Billings | 606/41 |
| 5,549,605 | 8/1996 | Hahnen | 606/49 |
| 5,599,349 | 2/1997 | D'Amelio | 606/46 |

*Primary Examiner*—Lee S. Cohen
*Attorney, Agent, or Firm*—Lyon & Lyon LLP

[57] ABSTRACT

An improved electrode for use in medical procedures requiring tissue removal. At least one gear shaped element is provided and mounted onto a distal tip region of a wire loop electrode. The gear shaped element distributes current at a tissue/electrode interface and enables the electrode to cut through substantial quantities of tissue while simultaneously creating a substantial rim of coagulation within an area of cut tissue.

23 Claims, 7 Drawing Sheets

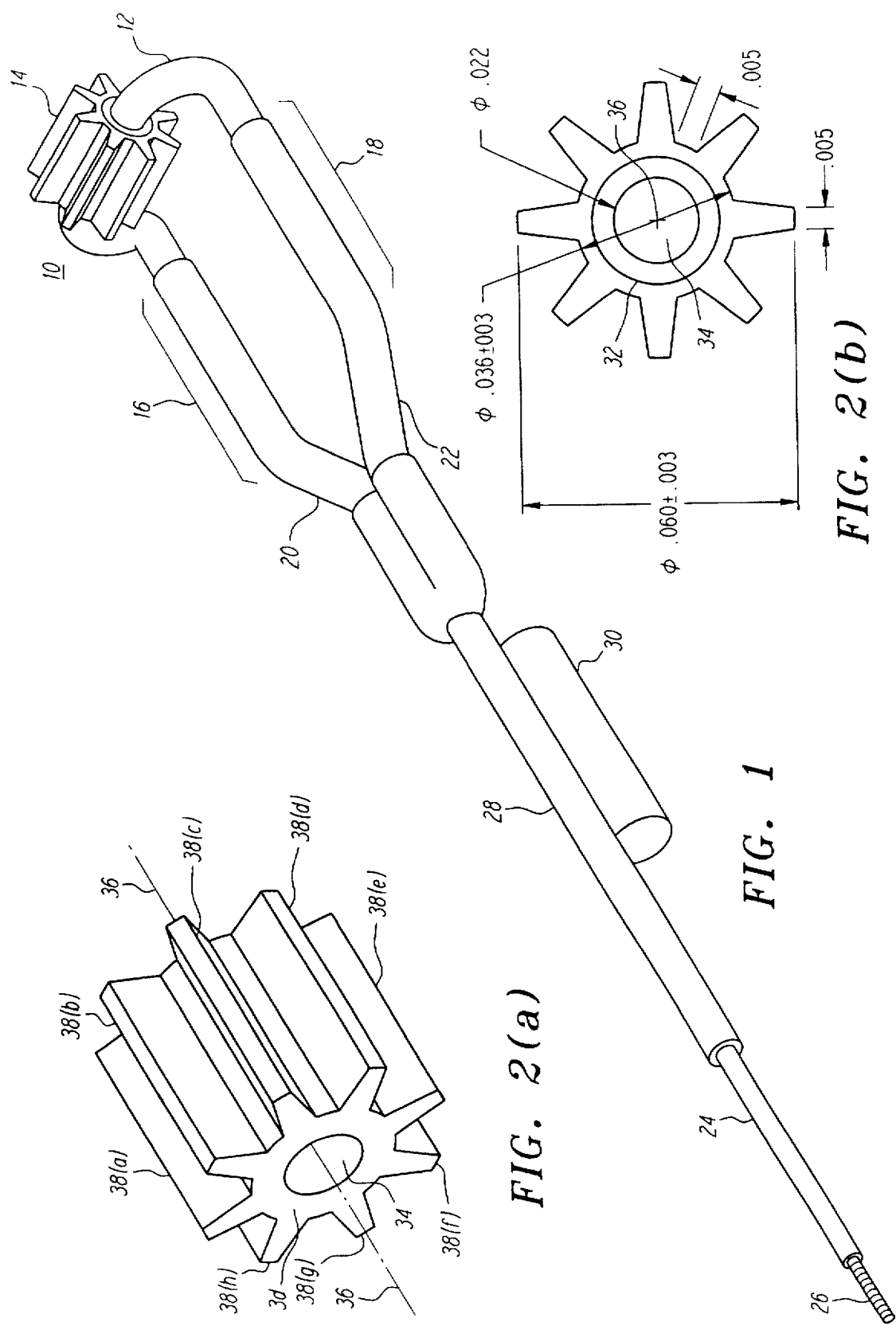

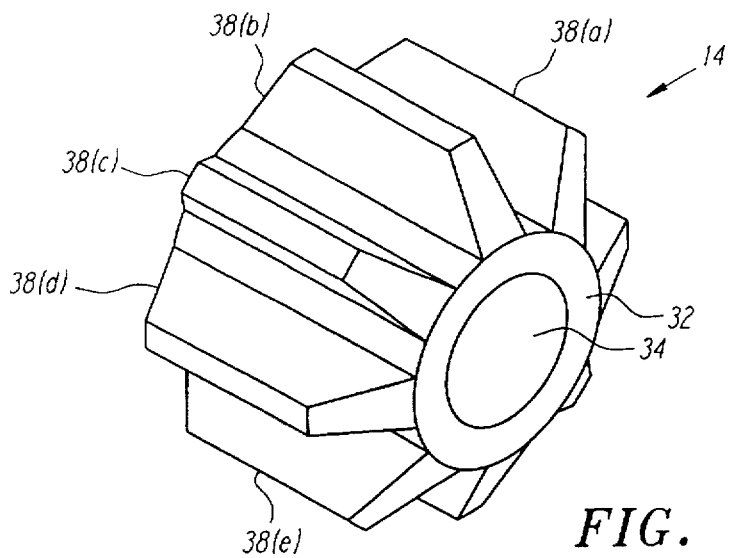
FIG. 3(a)
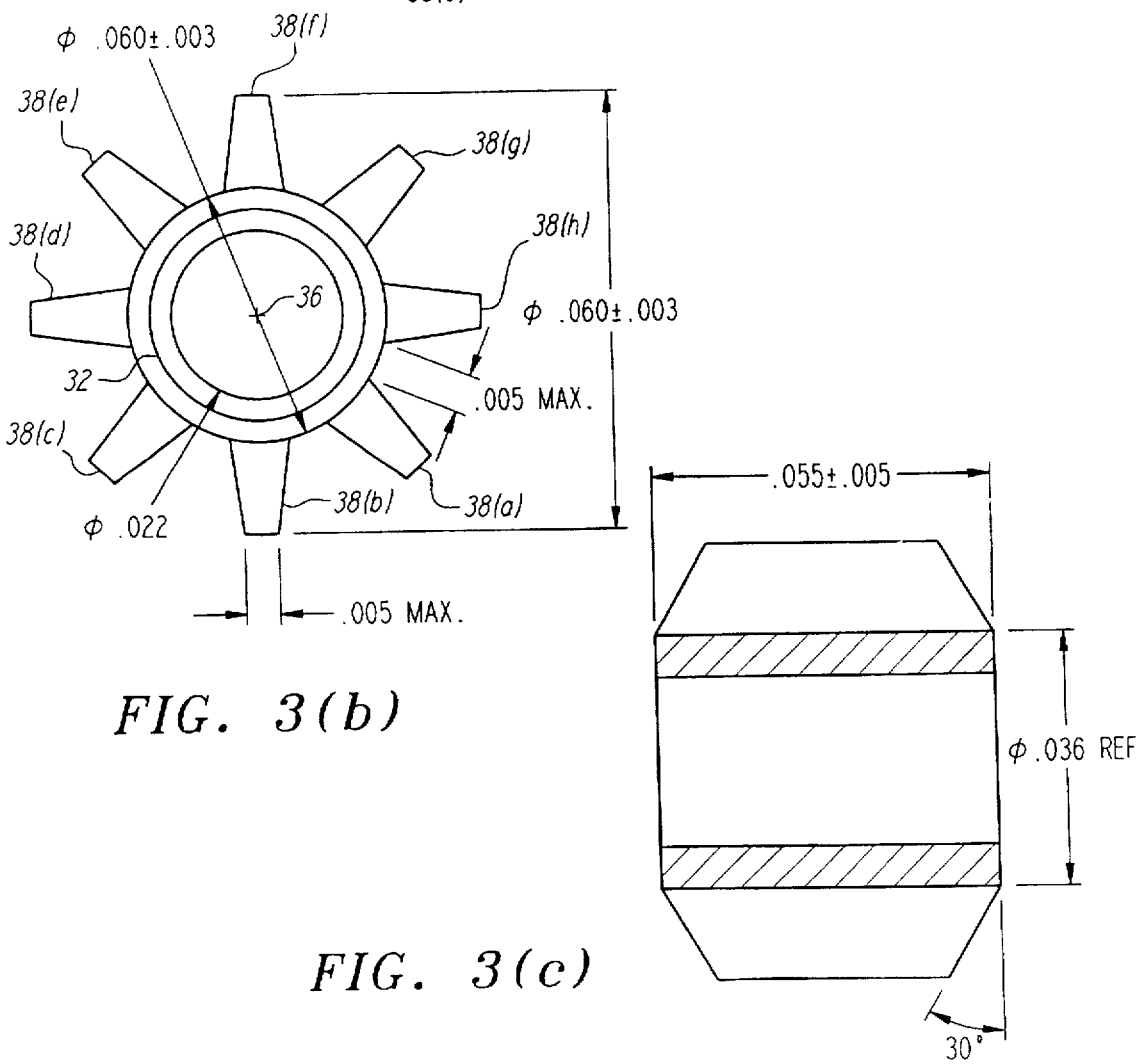
FIG. 3(b)
FIG. 3(c)

ELECTROSURGICAL LOOP PROVIDING ENHANCED TISSUE COAGULATION

BACKGROUND OF THE INVENTION

The field of the present invention is electrosurgical tools and, in particular, electrosurgical tools for cutting and coagulating tissue.

Electrosurgical tools are used in many medical procedures to remove unwanted or diseased tissue. For example, in urological procedures resectoscopes equipped with wire loop electrodes are often used to perform transurethral prostate resections. Conventional resectoscopes, such as those described in U.S. Pat. No. 5,196,011, entitled "Cutting Electrode for Medical Resectoscope," and U.S. Pat. No. 4,917,082, entitled "Resectoscope Electrode," generally employ an electrode assembly having the form of a U-shaped tungsten wire loop (hereinafter a "loop electrode") to remove, ablate or scar designated tissue areas. While these devices cut through tissue very effectively, they provide little, if any, coagulation in an area of cut tissue. Moreover, when an incision or cut in an area of tissue is formed using a conventional electrosurgical loop, blood vessels within and underlying the incision are often severed, and bleeding often results. One way to control this bleeding, is to heat the tissues surrounding the incision and, in doing so, to induce coagulation of the blood within those surrounding tissues. Accordingly, when a conventional wire loop is used to cut through an area of tissue, heating of the tissues surrounding the cut is often effected by passing the loop over the site of the cut for a second time. However, effecting tissue coagulation in this manner can be a difficult task.

In an effort to control bleeding during electrosurgical procedures, conventional loop electrodes have been modified in many ways. For example, it has been found that by mounting a "roller ball" or "roller bar" on the tip of a conventional loop, the current density provided by the loop at a point of tissue contact may be reduced, and the capability of a conventional loop to provide tissue coagulation may be greatly enhanced. Indeed, in many instances it has been found that the coagulation provided by roller bar or roller ball electrodes is so substantial that bleeding is effectively eliminated. Unfortunately, the use of roller balls and roller bars on conventional loops substantially inhibits the ability of those loops to cut through tissue. Moreover, when electrodes equipped with roller balls or roller bars are used to remove tissue, the tissue must often be ablated one layer at a time, thus making the removal of substantial quantities of tissue a difficult task. Exemplary loops employing roller balls and roller bars are shown in U.S. Pat. No. 5,354,296, entitled "Electrocautery Probe With Variable Morphology Electrode," and U.S. Pat. No. 5,395,363, entitled "Diathermy Coagulation and Ablation Apparatus and Method."

Because it would be quite advantageous in many medical applications to utilize an electrosurgical loop having the ability to cut through substantial quantities of tissue while providing substantial coagulation in a single pass through a tissue site, a new electrode for use in electrosurgical procedures is desired.

SUMMARY OF THE INVENTION

The present invention is directed to an improved electrode for use in electrosurgical procedures, a resectoscope employing such an electrode, and methods of using such an electrode.

In one embodiment, an electrode in accordance with the present invention may comprise a wire loop having at least one gear shaped element rotatably mounted thereon. The gear shaped element functions to distribute the current applied by the electrode at the tissue/electrode interface and, thus, to reduce the density of the current applied at that interface. This allows the electrode to create a rim of coagulation in an area of tissue, as the electrode passes through that area. Further, it may be noted that the reduction of the density of the current applied at the tissue/electrode interface is not substantial enough to impair the cutting capabilities of the electrode. Thus, an electrode in accordance with the present invention may cut through an area of tissue and, simultaneously, create a rim of coagulation within that tissue area. This enables an electrode in accordance with the present invention to minimize unwanted bleeding while cutting through substantial quantities of tissue.

As will be explained more fully below, the gear shaped element may comprise, for example, a core region and at least one thread element, wherein the at least one thread element extends outwardly from the core region. In one preferred form, the gear shaped element may comprise a plurality of thread elements which extend along a length of the core region in a direction parallel to a central axis of the core region. In another preferred form, the gear shaped element may comprise a single thread element which extends along a length of the core region and wraps around a portion of the core region, in a fashion similar to a thread wrapping around the body of a screw.

Accordingly, it is an object of the present invention to provide for use in electrosurgical procedures an electrode which has the ability to cut through substantial quantities of tissue while simultaneously providing a substantial rim of coagulation within an area of cut tissue.

It is another object of the present invention to provide an improved resectoscope for use in electrosurgical procedures including, but not limited to, transurethral prostate resection surgery.

It is still another object of the present invention to provide improved methods for performing electrosurgical procedures including, but not limited to, transurethral prostate resection surgery.

BRIEF DESCRIPTION OF THE DRAWINGS

FIG. 1 provides an illustration of an electrode in accordance with one form of the present invention.

FIG. 2(a) provides an illustration of a gear shaped element which may be mounted onto a wire loop electrode in accordance with one preferred form of the present invention.

FIG. 2(b) is a cross-sectional view of the gear shaped element illustrated in FIG. 2(a).

FIG. 3(a) provides an illustration of a gear shaped element in accordance with a second preferred form of the present invention.

FIG. 3(b) is a cross-sectional view of the gear shaped element illustrated in FIG. 3(a).

FIG. 3(c) is an illustration of the gear shaped element illustrated in FIG. 3(a).

3

Figure 6A:
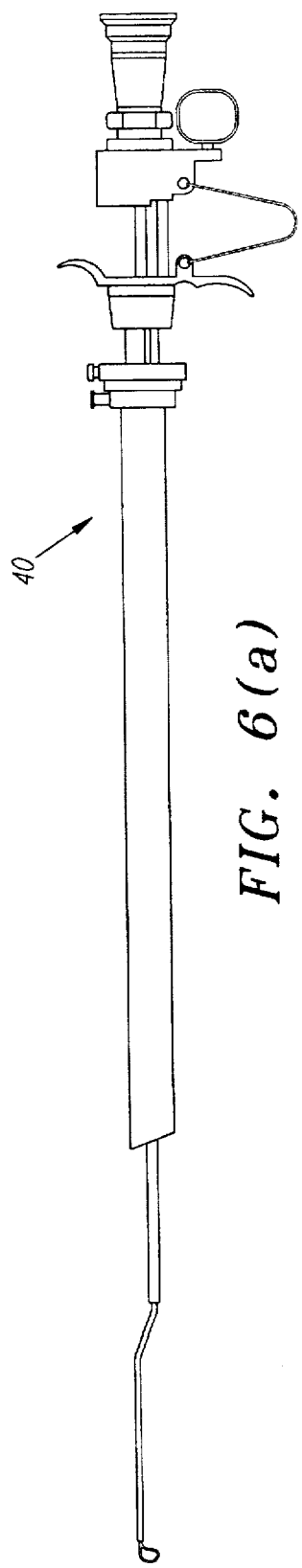

FIG. 6(a) provides an illustration of a resectoscope in accordance with the present invention.

Figure 6B:
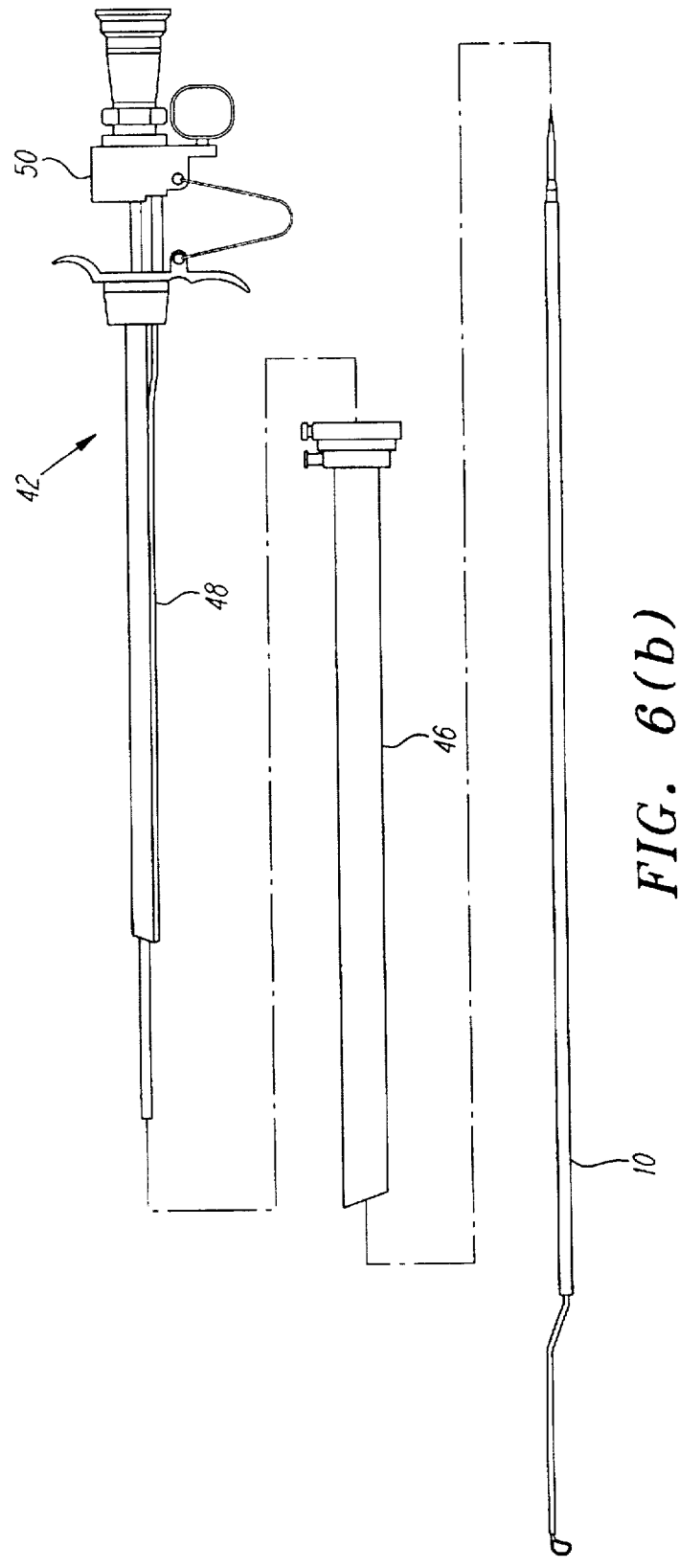

FIG. 6(b) provides an illustration of a plurality of elements comprising a resectoscope in accordance with the present invention.

Figure 7A:
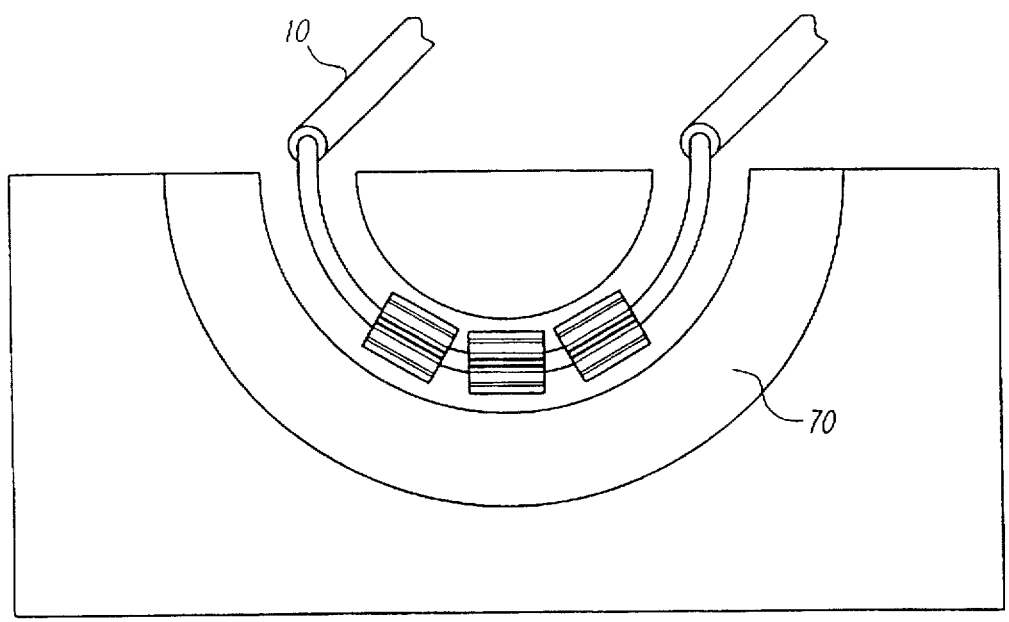

FIG. 7(a) provides an illustration of a rim of coagulation which may be formed as an electrode in accordance with the present invention cuts through a tissue site.

Figure 7B:
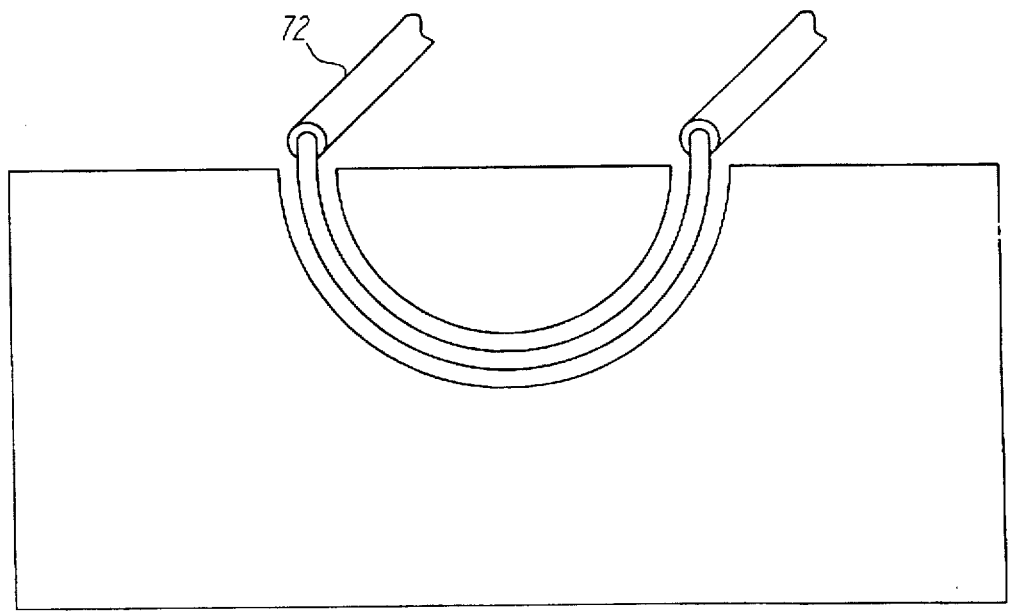

FIG. 7(b) illustrates the inability of conventional loop electrodes to create a rim of coagulation within an area of cut tissue.

Figure 7C:
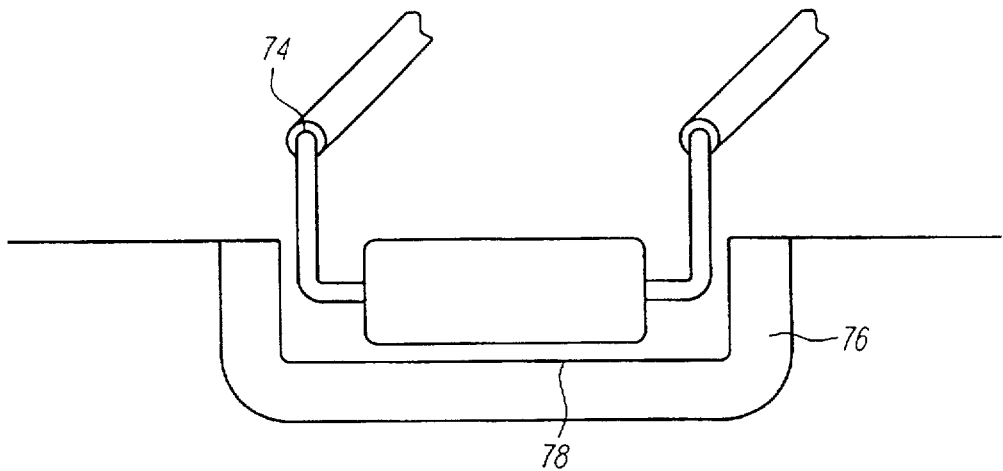

FIG. 7(c) illustrates the function of a conventional roller bar electrode.

DESCRIPTION OF THE PREFERRED EMBODIMENTS

Turning now to the drawings, FIG. 1 provides an illustration of an electrode 10 in accordance with one form of the present invention. As shown, the electrode 10 comprises a wire loop 12 which has a gear shaped element 14 rotatably mounted thereon. A pair of support wires 16 and 18, which are substantially enclosed within insulating sleeves 20 and 22, extend from opposite ends of the wire loop 12. The insulating sleeves 20 and 22 may comprise heat shrinkable tubes made of Teflon®, Kynar® or any of a number of other insulating materials. The support wires 16 and 18 are coupled in turn to the distal end of a single stainless steel wire electrode stem 24. The electrode stem 24 has an electrical connector 26 formed at its proximal end and, like support wires 16 and 18, the electrode stem 24 is substantially enclosed within a sleeve of insulation 25. In a preferred form, the electrode stem 24 and a portion of the support wires 16 and 18 are encased within a stainless steel stabilizer 28, and a mount 30 for a telescope (or endoscope) is fixed to the stabilizer 30.

The manufacture of wire loops, such as the wire loop 12 illustrated in FIG. 1, is well known in the art, and wire loops manufactured from tungsten or stainless steel wire are presently preferred. As for the gear shaped element 14, it is presently preferred that the gear shaped element 14 be machined from stainless steel, and it is believed that American Swiss Machining, Inc. of Rochester, N.Y. and North Shore Tool and Gear of Long Island, N.Y., have the capabilities to manufacture the gear shaped elements 14 shown in FIGS. 1–5.

Now, turning to FIGS. 2(a) and 2(b), in a preferred form the gear shaped element 14 may comprise a central core 32 having a cylindrical hole 34 formed through its center and along its central axis 36, and having a plurality of thread elements 38(a)–(h) extending from its exterior surface. In a presently preferred form, the central core may have an external diameter of approximately 0.036 inches, the hole 34 formed through the central core 32 may have a diameter of approximately 0.022 inches, and the thread elements 38(a)–(h) may have a height of approximately 0.012 inches, a length of approximately 0.055 inches, and a tip width of approximately 0.005 inches.

In an alternative embodiment shown in FIGS. 3(a)–3(c), the dimensions of the gear shaped element 14 may be modified by bevelling the side edges of the thread elements 38(a)–(h) at an angle, for example, a 30° angle.

Figure 4A:
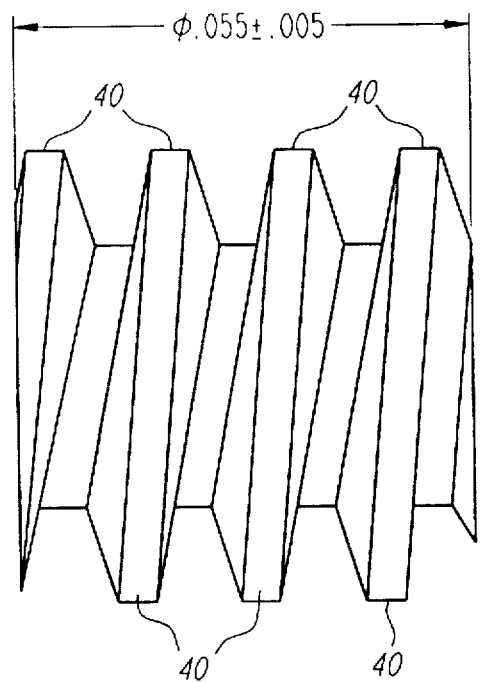
FIG. 4(a) provides an illustration of a gear shaped element in accordance with a third preferred form of the present invention.
Figure 4B:
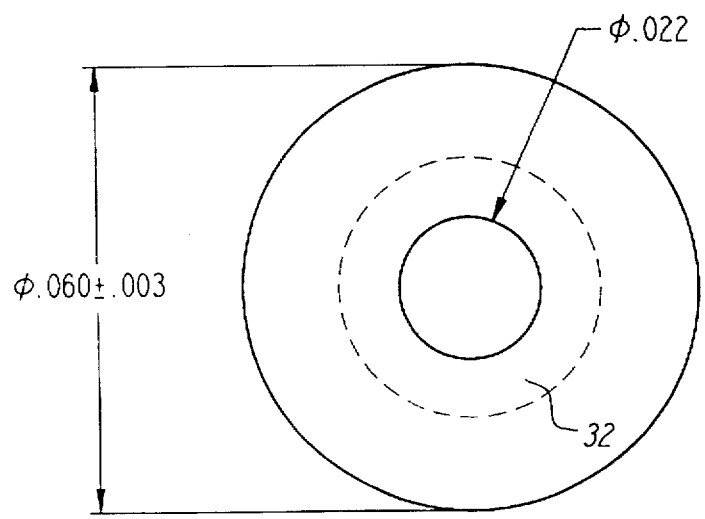
FIG. 4(b) is a cross-sectional view of the gear shaped element illustrated in FIG. 4(a).

In yet another embodiment shown in FIGS. 4(a) and 4(b), the gear shaped element 14 may comprise a central core 32, such as that described above, and a thread element 40 which extends from and wraps around the central core 32, just as the thread (or threads) of a screw wrap(s) around the body of the screw. In this embodiment, the central core 32 may again have an external diameter of approximately 0.036 inches, and the thread element 40 may have a height of approximately 0.012 inches and a tip width of approximately 0.005 inches.

Figure 5:
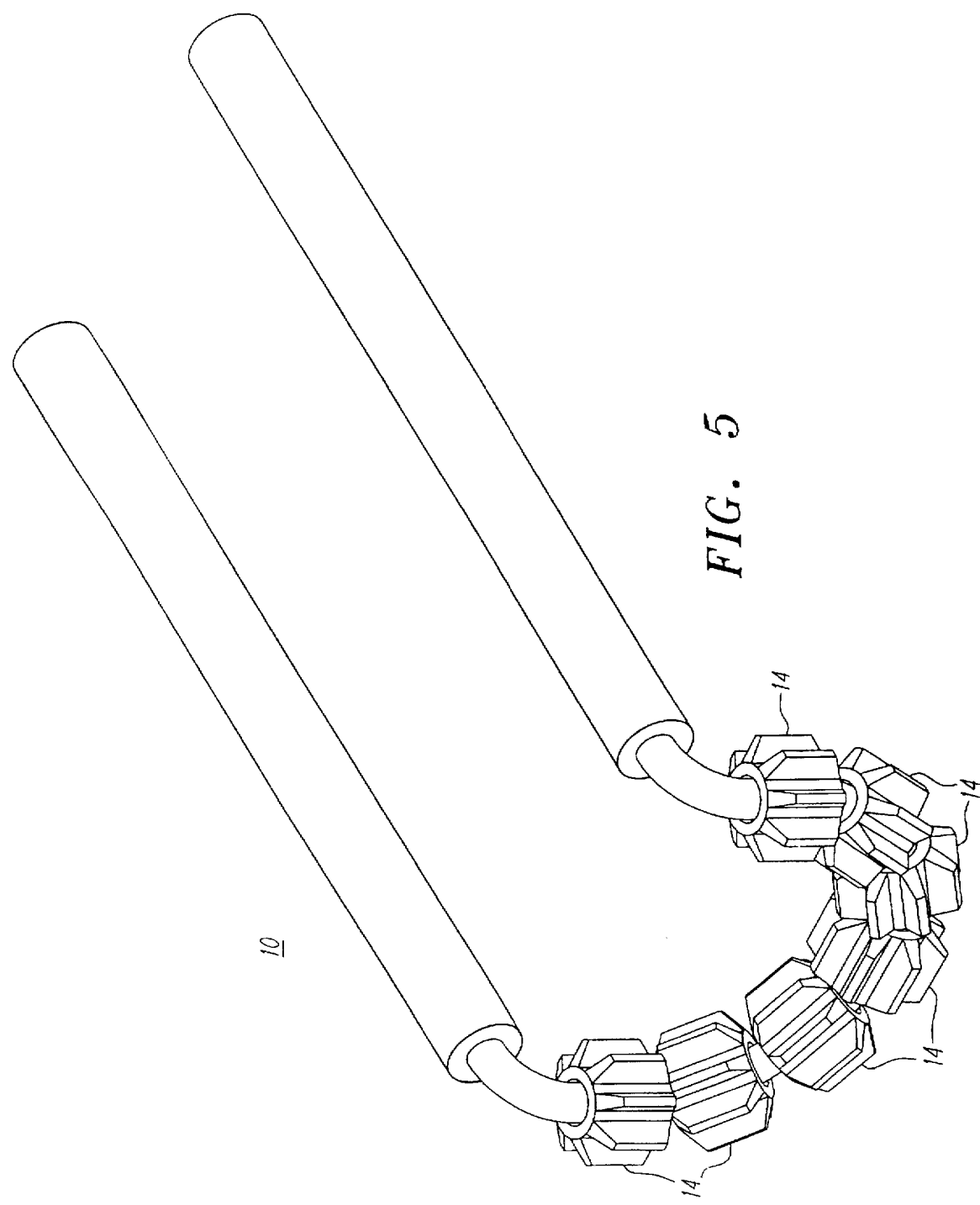
FIG. 5 provides an illustration of a wire loop electrode having multiple gear shaped elements mounted thereon in accordance with the present invention.

As shown in FIG. 5, for some electrosurgical applications it may be preferred to mount a plurality of gear shaped elements, such as those described above, on a single wire loop 12. For example, where an electrode 10 in accordance with the present invention may be used to perform transurethral prostate resections, it is presently believed to be desirable to mount 5 of the gear shaped elements 14 on the wire loop 12.

Those skilled in the art will appreciate that the dimensions of the gear shaped elements 14 may vary substantially and that only presently preferred dimensions of the gear shaped elements 14 are disclosed herein. Further, it will be noted that a single gear shaped element having an extended length could replace the multiple gear shaped elements 14 illustrated in FIG. 5.

Turning now to FIGS. 6(a) and 6(b), a resectoscope 40 in accordance with the present invention may comprise an electrode 10 (such as that illustrated above), a working element 42, a telescope 44, and a sheath 46. During use the electrode 10 and the telescope 44 are inserted within the barrel 48 of the working element 42, and the barrel 48 of the working element 42 is inserted within the sheath 46. The electrode 10 and telescope 44 are also releasably coupled to a sliding element 50 of the working element 42, such that the tip 52 of the electrode 10 may be extended from and retracted into the barrel 48 under the control of the sliding element 50. The manufacture and use of resectoscopes is well known in the art, and it is presently preferred to utilize resectoscopes such as those manufactured by CIRCON ACMI, of Stanford, Conn. (Model Nos. DP29-0002-104 and DP29-0002-101) with the electrodes of the present invention.

Turning now to FIGS. 7(a)–7(c), as was explained somewhat briefly in the introductory sections above, an electrode 10 in accordance with the present invention has the ability to cut through substantial quantities of tissue while simultaneously creating a substantial rim of coagulation 70 within an area of cut tissue. This is illustrated in FIG. 7(a). In contrast, prior art electrodes such as the conventional loop 72, shown in FIG. 7(b), and the conventional "roller bar" 74 shown in FIG. 7(c) do not provide this capability. Moreover, as a conventional loop 72 cuts through an area of tissue, large quantities of tissue may be removed, but little (if any) coagulation is induced within the surrounding tissues. The opposite is true for the conventional roller bar 74. Moreover, as a roller bar 74 is pulled over the surface of an area of tissue, a substantial rim of coagulation 76 is formed within the underlying tissue, but only the surface tissue 78 is removed.

To perform tissue removal and, in particular, to perform transurethral prostate resections using an electrode 10 in accordance with the present invention, it is preferable to couple the electrode 10 (described above) to an electrosurgical generator capable of providing in a tissue cutting mode 300 watts of power at a load of 300 ohms. Exemplary electrosurgical generators of this type are the Force 30 and Force 40S generators manufactured by Valleylab, Inc. of Boulder, Colo. As it is believed that the use of these electrosurgical generators is well known in the art, their use will not be described herein in detail. However, it should be noted that when used with an electrode in accordance with the present invention to perform simultaneous tissue removal and coagulation, it is presently preferred to configure the Force 30 and Force 40S electrosurgical generators in "cut" mode, and to apply power to the electrode 10 as needed. In cut mode, the Valleylab electrosurgical generators described above will provide an output having a maximum open circuit voltage of 3300 V, a maximum power of 300 watts, and a frequency of 500 kHz (sinusoidal waveform) at a load of 300 ohms. When power is applied in this manner to an electrode 10 in accordance with the present invention, the electrode 10 may be used to cut through a substantial quantity of tissue (as shown in FIG. 7(a)) and to simultaneously create a substantial zone of coagulation within that tissue.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. An apparatus for use with an electrosurgical loop, wherein said apparatus enables said electrosurgical loop to induce substantial coagulation in an area of tissue as said electrosurgical loop cuts through said area of tissue, said apparatus comprising:

a gear shaped element capable of being rotatably mounted on and maintaining electrical communication with said electrosurgical loop;

said gear shaped element comprising a core region and at least one thread element, said at least one thread element extending outwardly from said core region, and said gear shaped element having a maximum diameter less than 0.06 inches.

2. The apparatus of claim 1, wherein said gear shaped element comprises a plurality of thread elements which extend along a length of said core region in a direction parallel to a central axis of said core region.

3. The apparatus of claim 2 wherein said core region has an external diameter of approximately 0.036 inches, and said thread elements have a height of approximately 0.012 inches, a length of approximately 0.055 inches, and a tip width of approximately 0.005 inches.

4. The apparatus of claim 3, wherein said thread elements have a pair of side surfaces which are bevelled at a predetermined angle.

5. The apparatus of claim 4, wherein said predetermined angle is 30°.

6. The apparatus of claim 1, wherein said gear shaped element is formed from stainless steel.

7. An electrode for use in electrosurgery, said electrode comprising:

a wire loop having at least one gear shaped element mounted thereon;

said at least one gear shaped element comprising a core region and at least one thread element, said at least one thread element extending outwardly from said core region; and said at least one gear shaped element having a diameter less than 0.06 inches.

8. The electrode of claim 7, wherein said at least one gear shaped element comprises a plurality of thread elements which extend along a length of said core region in a direction parallel to a central axis of said core region.

9. The electrode of claim 8 wherein said core region has an external diameter of approximately 0.036 inches, and said thread elements have a height of approximately 0.012 inches, a length of approximately 0.055 inches, and a tip width of approximately 0.005 inches.

10. The electrode of claim 9, wherein said thread elements of said at least one gear shaped element have a pair of side surfaces which are bevelled at a predetermined angle.

11. The electrode of claim 10, wherein said predetermined angle is 30°.

12. An electrode for use in electrosurgical procedures, said electrode comprising:

a wire loop having a first end region, a second end region and a body region;

at least one gear shaped element rotatably mounted on said body region of said wire loop, and having a diameter less than 0.06 inches;

a pair of support wires, each extending from one end of said wire loop, said support wires being substantially enclosed within first and second insulating members;

an electrode lead electronically coupled to said support wires, said electrode lead being substantially enclosed within a third insulating member and having one end which forms an electrical connector for coupling to a power cord;

a stabilizing element formed around a portion of said support wires and a juncture between said support wires and said electrode lead; and a telescope mount fixed to an exterior surface of said stabilizing element.

13. The electrode of claim 12, wherein said at least one gear shaped element comprises a core region and a plurality of thread elements, said thread elements extending outwardly from said core region, along a length of said core region, and in a direction parallel to a central axis of said core region.

14. The electrode of claim 13 wherein said core region has an external diameter of approximately 0.036 inches, and said thread elements have a height of approximately 0.012 inches, a length of approximately 0.055 inches, and a tip width of approximately 0.005 inches.

15. The electrode of claim 14, wherein five gear shaped elements are rotatably mounted on said body region of said wire loop.

16. The electrode of claim 15, wherein said thread elements of said five gear shaped elements each have a pair of side surfaces which are bevelled at a predetermined angle.

17. The electrode of claim 16, wherein said predetermined angle is 30°.

18. A resectoscope comprising:

a telescope;

an electrode assembly adapted to slidably engage said telescope;

a working element adapted to slidably receive said telescope and electrode assembly, said working element engaging said electrode assembly and providing a mechanism for slidably moving said electrode assembly along a central axis of said working element and in a field of view of said telescope; and a sheath adapted to slidably receive and engage said working element;

said electrode assembly comprising a wire loop having at least one gear shaped element mounted thereon, said at least one gear shaped element having a diameter less than 0.06 inches and comprising a core region and at least one thread element, and said at least one thread element extending outwardly from said core region.

19. The resectoscope of claim 18, wherein said at least one gear shaped element comprises a plurality of thread elements which extend along a length of said core region in a direction parallel to a central axis of said core region.

20. The resectoscope of claim 19 wherein said core region has an external diameter of approximately 0.036 inches, and said thread elements have a height of approximately 0.012 inches, a length of approximately 0.055 inches, and a tip width of approximately 0.005 inches.

21. An electrode for use in electrosurgical procedures, said electrode comprising:

loop means for cutting, ablating and coagulating bodily tissue, said loop means having a first end region, a second end region and a body region, and said loop means having at least one gear shaped current distribution means for distributing a current provided to said loop means, said gear shaped current distribution means being rotatably mounted on said body region, and such gear shaped current distribution means having a diameter less than 0.06 inches;

a pair of support means, each support means extending from and being in electrical communication with one end of said loop means;

lead means electronically coupled to said support means for providing power to said loop means, said lead means having one end which forms an electrical connector for coupling to a power source; and stabilizing means for providing increased rigidity to at least said lead means.

22. A method for removing unwanted bodily tissue comprising the steps of:

positioning a wire loop electrode having at least one gear shaped element rotatably mounted thereon adjacent an area of tissue to be removed, said gear shaped element having a diameter less than 0.06 inches;

delivering power to said wire loop electrode; and causing said wire loop electrode to pass through said area of tissue to be removed, whereby said wire loop electrode may create a rim of coagulation within said area of tissue as said wire loop electrode passes therethrough.

23. The method of claim 22 wherein said at least one gear shaped element comprises a core region and a plurality of thread elements which extend along a length of said core region in a direction parallel to a central axis of said core region;

said core region has an external diameter of approximately 0.036 inches; and said thread elements have a height of approximately 0.012 inches, a length of approximately 0.055 inches, and a tip width of approximately 0.005 inches.

* * * * *